US00PP36871P3

(12) United States Plant Patent
Bennett

(10) Patent No.: US PP36,871 P3
(45) Date of Patent: Aug. 5, 2025

(54) ***ROSA HYBRIDA* SHRUB PLANT NAMED 'AUSmajesty'**

(50) Latin Name: *Rosa hybrida*
Varietal Denomination: AUSmajesty

(71) Applicant: David Austin Roses Ltd., Wolverhampton (GB)

(72) Inventor: Carl Bennett, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 17/803,800

(22) Filed: Nov. 29, 2022

(65) Prior Publication Data

US 2025/0057059 P1 Feb. 13, 2025

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 5/0222
See application file for complete search history.

(56) References Cited

PUBLICATIONS https://www.helpmefind.com/rose/l.php?I=2.87394.1; Nov. 26, 2024; 1 page.*
CPVO Application Consultation Version 4.21.4 for 'AUSmajesty'; Nov. 26, 2024; 2 pages.*

* cited by examiner

*Primary Examiner* — Kent L Bell
(74) *Attorney, Agent, or Firm* — KPPB LLP

(57) ABSTRACT

A variety of rose plant of the shrub class, named 'AUSmajesty'. The 'AUSmajesty' is a variety of a rose bearing apple blossom pink rosettes which pale to a very soft pink, almost white color with a strong fragrance with hints of lemon sherbet and Old Rose, forming an exceptionally healthy shrub, which maintains a well-rounded shape.

1 Drawing Sheet

Classification: The present invention relates to a new *Rosa hybrida* shrub of the market class 'English Rose'.

Variety denomination: The new plant has the varietal denomination 'AUSmajesty'.

Origin of invention: This invention relates to a new and distinct variety of shrub rose plant named 'AUSmajesty', which was originated from the cross-pollination of the two 'unnamed' and unpatented seedlings of *Rosa hybrida.*

BACKGROUND OF THE INVENTION

The primary objective of this breeding was to produce a rose bearing apple blossom pink rosettes which pale to a very soft pink, almost white color with a strong fragrance with hints of lemon sherbet and Old Rose, forming an exceptionally healthy shrub, which maintains a well-rounded shape.

SUMMARY OF THE INVENTION

Among the features which distinguish the new variety from others presently available and commercial rose cultivars known to the inventor is the following combination of characteristics: soft pink blooms, paling to a blush pink, rosette shaped blooms, strong fragrance of lemon sherbet and Old Rose, in a large shrub that repeatedly flowers and has central bracts present.

Asexual reproduction of the new variety by budding as performed in Albrighton, United Kingdom shows that the foregoing and other distinguishing characteristics come true to form and are established and transmitted through succeeding asexual propagations. 'AUSmajesty' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSmajesty' are two unnamed seedlings. The new rose may be distinguished from its seed parent, by the following combination of characteristics: the seed parent is mauve in color compared to the pink of 'AUSmajesty', has larger flowers, more informal blooms, and more upright growth when compared to seed parent. The new rose may be distinguished from its pollen parent, by the following combination of characteristics: the pollen parent has a larger, more cupped bloom and has a growth of habit of a climbing rose as opposed to 'AUSmajesty', and is also less disease resistant.

COMPARISON WITH THE CLOSEST COMMERCIALLY AVAILABLE CULTIVAR

The most similar rose variety is 'AUSearnshaw' (U.S. Plant Pat. No. 31,400, granted 28 Jan. 2020). Both blooms are predominantly soft pink in color, however 'AUSearnshaw' has more petals per bloom (approx. 105) than 'AUSmajesty' (approx. 85-90). 'AUSearnshaw' also has considerably fewer number of blooms per lateral when compared to 'AUSmajesty'. The flower shape is also different, with 'AUSearnshaw' having a rounded bloom, whereas 'AUSmajesty' has a more irregularly rounded bloom. Finally, another notable difference relates to the quantity of prickles, with 'AUSearnshaw' having considerably fewer prickles present than 'AUSmajesty', which has a medium to high quantity.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSmajesty' specimens were made at a garden in Albrighton, Wolverhampton, United Kingdom. The following description is of 6-year-old rose plants of the new variety grown in a garden environment in Albrighton, United Kingdom in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 3.2 cm long and 1.8 cm in diameter when the petals start to unfurl.

*Form*.—The bud form is long pointed ovoid.

*Color*.—When sepals first divide, the bud color is RHS 67A to RHS 68A (red-purple group). When half blown, the upper sides of the petals are RHS 65D (red-purple group), and the lower sides of the petals RHS 65D (red-purple group).

*Calyx*.—Shape: star shape, with the sepals folding back against the stems. Length: 7 cm. Diameter: 7 cm.

*Sepals*.—Arrangement: Regularly arranged. Color: Upper Surface: RHS N144B (yellow-green group) with occasional spots or streaks of RHS 63A (red-purple group). Lower Surface: RHS 143C (yellow-green group) with a central vertical stripe of RHS 63A (red-purple group). Length: 2.8 cm. Width: 0.9 cm. Shape: Lanceolate. Margin: Glandular. Surface texture: Upper Surface: Hairy. Lower Surface: Smooth. Number: There are 2-3 lightly appendaged sepals, and 2-3 unappendaged sepals with glandular edges.

*Receptacles*.—Color: Predominately RHS 146C (yellow-green group) with flashes of RHS 71B (red-purple group). Shape: Pear. Size: Small, about 0.6 cm long×0.6 cm wide. Surface: Smooth.

*Peduncle*.—Length: Short, averaging about 3.6 cm. Surface: Smooth. Color: Irregular mix of RHS 145A (yellow-green group) with RHS 60A (red-purple group). Strength: Normal.

Blooms:

*Size*.—Medium, average open diameter is about 8 cm and average depth is about 2.8 cm.

*Borne*.—Several together in clusters of 5-10 with blooms having an irregular shape.

*Penduncle*.—Strength: Normal, average length is about 3.6 cm. Diameter: 0.2 cm.

*Form*.—When first open, bloom is cupped. Permanence of bloom flattens: outer petals curl slightly.

Petalage: Number of petals under normal conditions: 85-90.

*Color*.—The upper sides of the petals are RHS 65C (red-purple group). The reverse sides of the petals are RHS 65C (red-purple group). The base of the petals has a medium yellow spot that is RHS 11B (yellow group) in color.

*Variegations*.—None.

*Discoloration*.—The general tonality at the end of the first day is RHS 62C (red-purple group), and at the end of the third day is RHS 65D (red-purple group). As bloom ages, color pales further to approximately RHS 69B (red-purple group).

*Fragrance*.—Strong. Character of fragrance: Lemon Sherbet/Old Rose.

Petals:

*Texture*.—Smooth, satiny and thin on both sides.

*Size*.—Width: 2.8 cm. Length: 4 cm.

*Surface*.—Smooth.

*Shape*.—Oval of inner petals and obcordate of outer petals.

*Margin*.—Entire.

*Apex shape*.—Orbicular/Rounded.

*Base shape*.—Accuminate.

*Form*.—Tips slightly recurved.

*Arrangement*.—Informal.

*Petaloids*.—Number: up to 5. Color: RHS 65C (red-purple group). Length: 1.2 cm. Width: 0.6 cm. Shape: Obovate. Margin: Uniform.

*Persistence*.—Petals hang on and dry.

*Lastingness*.—On the plant: Long/Fair about 7 days. As a cut flower: not tested.

Reproductive parts:

*Stamens*.—Number: approximately 10-15. Length: approximately 0.9 cm.

*Anthers*.—Length: approximately 0.25 cm. Color: RHS 13B (yellow group). Arrangement: Regular around styles.

*Filaments*.—Color: RHS 59C (red-purple group). Length: 0.7 cm.

*Pollen*.—Quantity: Moderate. Color: RHS 10A (yellow group).

*Pistils*.—Number: approximately 20. Length: approximately 0.75 cm.

*Styles*.—Color: RHS 2D (yellow group). Length: 0.6 cm.

*Stigmas*.—Color: RHS 13B (yellow group) with a slight touch of red (too slight to measure effectively). Length: approximately 0.1 cm.

*Hips*.—NONE Observed.

PLANT CHARACTERISTICS

Plant form: Shrub.

Plant growth: Vigorous and branching.

Age to maturity: 2 years.

Mature plant: Height: 150 cm. Width: 150 cm.

Rootstock: '*Rosa dumetorum* 'Laxa' for the observed plants in the United Kingdom. 'Dr Huey' in the USA.

Foliage:

*Number*.—Leaflets on normal mid-stem leaves is: 5 with instances of 7 (including terminal leaflet).

*Size*.—Medium, about 17.5 cm long×10.5 cm wide.

*Quantity*.—Abundant. Number of leaves per flowering stem is: approximately 10.

*Color*.—New foliage: Upper side: RHS 144A (yellow-green group). Lower side: RHS 146C (yellow-green group). Old foliage: Upper side: RHS 137A (green group). Lower side: RHS 147B (yellow-green group).

Leaflets:

*Size*.—About 5.5 cm long×4 cm wide.

*Shape*.—Pointed oval.

*Base shape*.—Cordate.

*Apex shape*.—Acuminate.

*Texture*.—Upper side: Leathery. Lower side: Leathery.

*Edge*.—Serrated.

*Serrations*.—Small.

*Petiole*.—Color: central upper side is RHS 184C (greyed-purple group), and outer upper and reverse side are RHS 144C (yellow-green group). Length: 4.4 cm. Width: 0.2 cm. Surface Texture: Glandular.

*Petiole rachis*.—Color: ventral upper side RHS 184C (greyed-purple group), and outer upper and reverse sides are RHS 144C (yellow-green group). Underside: smooth with prickles.

*Stipules*.—Length: 3 cm. Shape: Lateral. Descriptor: serrated to slightly glandular. Apex: Acute. Color: RHS N144D (yellow-green group).

*Auricle*.—Shape: Lanceolate. Length: 1 cm. Width: 0.4 cm. Color: RHS N144D (green group).

*Vein color*.—RHS 137A (green group).

*Venation pattern*.—Reticulate.

Wood:

*New wood*.—Color: RHS 59A (red-purple group) with flashes of RHS 144B to RHS 144C (yellow-green group). Bark: Smooth.

*Old wood*.—Color: RHS 143C (green group). Bark: Smooth.

Branching habit:

*Number*.—4-5 per main stem.

*Dimensions*.—Length: 80-100 cm. Diameter: 0.7 cm-0.8 cm.

Stems:

*Mature stem*.—Length: 120 cm-150 cm. Diameter: approximately 1.2 cm.

*Internode distance*.—7 cm. The above measurements are all variable, depending on growing conditions in a season.

*Stem pubescence present*.—No.

Prickles:

*Quantity*.—On main canes from base: many/ordinary. Number per stem length: 10-15 per 20 cm. On laterals from main canes: many/ordinary. Number per stem length: 10-15 per 20 cm.

*Form*.—Straight to slightly concave.

*Length*.—0.8 cm.

*Color when young*.—Slightly transparent RHS 60A (red-purple group).

*Color when mature*.—RHS 199C (grey-brown group).

Small prickles:

*Quantity*.—Main stalk: Few. Number per stem length: 5 per 10 cm. Laterals: Few. Number per stem length: 5 per 10 cm.

*Color*.—When young: slightly transparent RHS 60A (red-purple group). When mature: RHS 199C (grey-brown group).

Disease resistance:

*Powdery mildew* (*Podosphaera pannosa*).—Resistant.

*Downy mildew* (*Peronospora species*).—Resistant.

*Blackspot* (*Diplocarpon rosae*).—Resistant.

*Rust* (*Phragmidium tuberculatum*).—Resistant.

Pest resistance: Not tested.

Winter hardiness: Not tested.

Growing conditions: Normal garden conditions.

What is claimed is:

1. A new and distinct variety of rose plant of the shrub class, named 'AUSmajesty', substantially as herein shown and described.

* * * * *

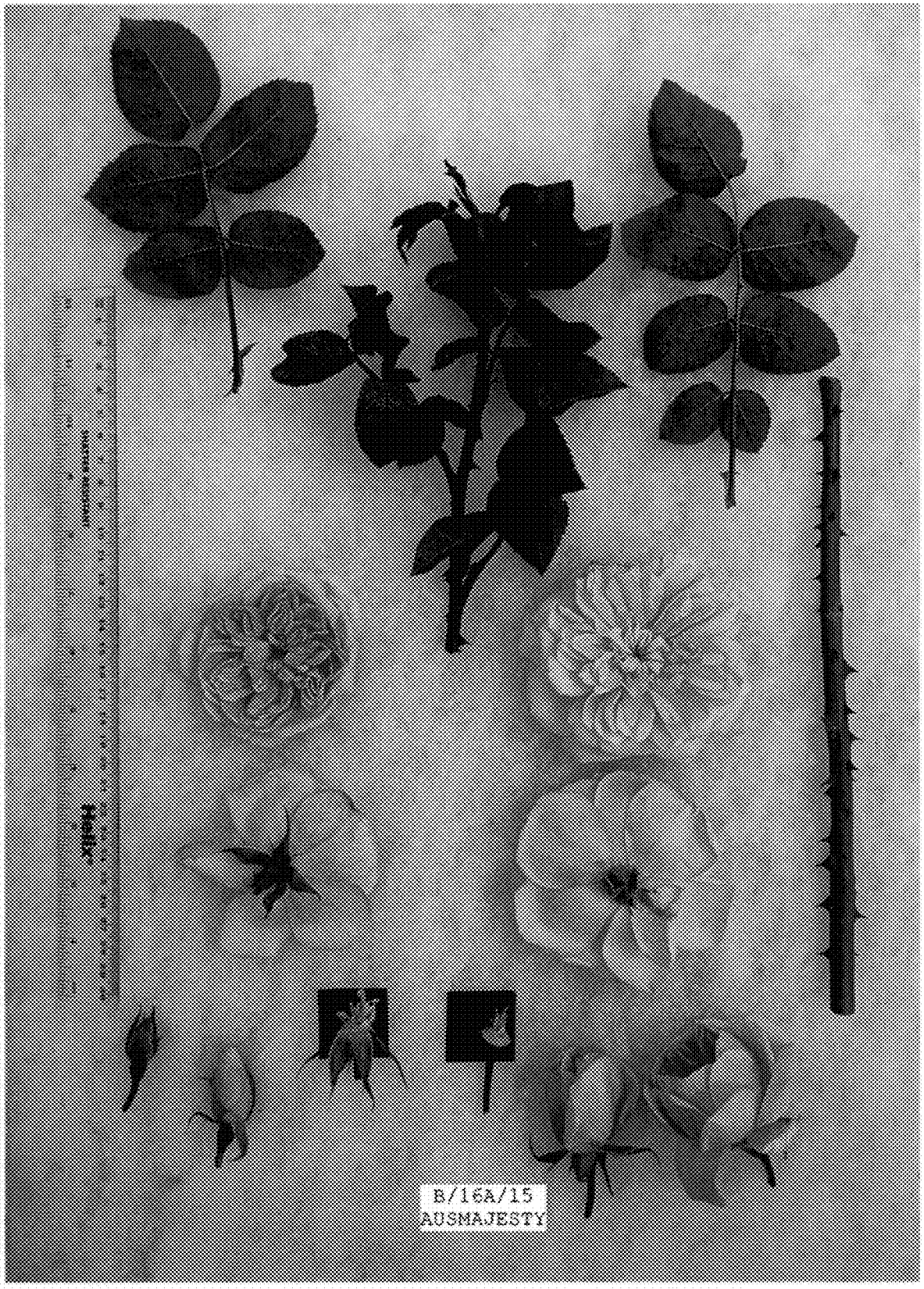
B/16A/15
AUSMAJESTY